United States Patent

Petersen

[11] 4,008,047
[45] Feb. 15, 1977

[54] BLOOD COMPATIBLE POLYMERS FOR BLOOD OXYGENATION DEVICES

[75] Inventor: Robert J. Petersen, Minneapolis, Minn.

[73] Assignee: North Star Research Institute, Minneapolis, Minn.

[22] Filed: Dec. 26, 1974

[21] Appl. No.: 536,397

[52] U.S. Cl. .................... 23/258.5 M; 210/321 B; 210/500 M; 128/DIG. 3
[51] Int. Cl.² .................... A61M 1/03; B01D 39/18
[58] Field of Search ............. 23/258.5 A, 258.5 M, 23/25.5 MA; 210/321 R, 500 M; 128/214; 3/1; 55/16

[56] References Cited

UNITED STATES PATENTS

| | | | |
|---|---|---|---|
| 2,980,491 | 4/1961 | Metairie et al. | 260/224 |
| 3,551,244 | 12/1970 | Forester et al. | 156/306 X |
| 3,592,672 | 7/1971 | Rowley et al. | 210/500 M |
| 3,592,953 | 7/1971 | Ward et al. | 210/500 M |
| 3,839,743 | 10/1974 | Schwarcz | 3/1 |
| 3,865,615 | 2/1975 | Manly | 3/1 |
| 3,878,109 | 4/1975 | Ikeda et al. | 210/500 M |

FOREIGN PATENTS OR APPLICATIONS 1,120,373 7/1968 United Kingdom

OTHER PUBLICATIONS

"Interactions of Materials with Blood", Ch. 3, pp. 73–118, Blood Compatible Synthetic Polymers, Bruck, 1974.

Primary Examiner—Morris O. Wolk
Assistant Examiner—Michael S. Marcus
Attorney, Agent, or Firm—Thomas M. Meshbesher

[57] ABSTRACT

Fluoroacylation of ethyl cellulose has been found to result in good gas permeability and blood compatibility for polymeric layers made from the resulting fluorinated esters. The fluoroacylated ethyl cellulose has good hydrolytic stability at blood pH and under sterilization conditions (e.g. 100° C). For use in blood oxygenation devices, implantable biomedical devices, blood sampling or analysis or purification devices, etc., it is preferred that the fluoroacylated ethyl cellulose be substantially free of residual OH and have a fluorine content above 10% by weight (e.g. at least about 12% by weight).

5 Claims, 2 Drawing Figures

BLOOD COMPATIBLE POLYMERS FOR BLOOD OXYGENATION DEVICES

The invention described herein was made in the course of work under a grant or award from the Department of Health, Education, and Welfare.

FIELD OF THE INVENTION

This invention relates to polymers which can be made into films, membranes, coatings, fibers, woven and non-woven layers, and similar structures, which structures have blood compatibility hydrolytic stability, and, preferably, gas permeability. An aspect of this invention relates to methods for using these polymers in devices or methods in which the blood of a living animal comes into contact with a non-living surface. Examples of such devices include blood oxygenators, biological implants (e.g. prostheses), catheters, cannulas, artificial kidneys or other artificial organs, blood filters, probes, and devices for sampling and analysis of blood. Another aspect of this invention relates to novel derivatives of ethyl cellulose.

DESCRIPTION OF THE PRIOR ART

It has long been recognized that an enormous variety of organic and inorganic foreign substances, when brought into contact with the blood of a living animal, will stimulate the formation of blood clots. However, it has only been relatively recently that the clotting or thrombogenic effect of foreign substances has been investigated very effectively from a theoretical standpoint. For example, the electronegative character of the endothelial wall of the circulatory system was not fully recognized until the 1950's. The study of interactions between plasma proteins and/or cellular elements of blood (e.g. platelets) and foreign substances is still far from comprehensive. A good summary of the present understanding of these phenomena is contained in Chapter III of *Blood Compatible Synthetic Polymers* by S. D. Bruck, published by C. C. Thomas, Springfield, Ill., 1974. Dr. Bruck also summarizes the still largely empirical approaches toward the syntheses of relatively blood-compatible (relatively non-thrombogenic) polymers.

As a general rule, the properties desired in a blood oxygenator membrane include: good gas permeability (at least with respect to gaseous oxygen and carbon dioxide); chemical stability (particularly at the blood pH of 7.4 and at temperatures within the range of 20° – 40° C., but preferably also at other pH's and temperatures used in sterilization (e.g. 100° C); blood compatibility or substantially non-thrombogenic behavior in blood-containing environments; sufficiently hydrophobic character to serve as a water vapor barrier; ease in manufacture (e.g. sufficient solubility to permit solvent casting or the like); non-toxicity; relative inertness to body fluids; and mechanical strength and handling properties adequate for facilitating the assembly and use of the blood oxygenation devices.

Unfortunately, it is difficult to combine non-thrombogenic behavior with other properties which are necessary or desirable in blood oxygenators. For example, attempts have been made to improve the blood compatibility of polydimethylsiloxane. This class of polymers, except for its adverse tendencies with respect to various blood components (absorption of lipids, promotion of platelet adhesion, and the like), can have some physical and chemical properties which are very useful in blood oxygenation devices, including good gas permeability. It has been suggested that side chains with negative polarity attached to the siloxane polymer backbone would improve the blood compatibility of this class of polymers, and partially fluorinated polysiloxanes have been synthesized and tested for both gas permeability and blood compatibility. The introduction of the fluorine-containing side chains resulted in "lowered permeability toward oxygen and carbon dioxide in comparison to polydimethylsiloxane and mixtures of polydimethylsiloxane and fluorinated polysiloxanes. Blood compatibility data for the fluorosiloxane elastomers suggest that the 65/35 mole percent blend of fluorosiloxane/dimethylsiloxane performs somewhat better than the fluorosiloxane homopolymer, despite the larger number of fluorine groups present in the latter" (S. D. Bruck, op. cit., page 76).

To further illustrate the problems of synthesizing or discovering the ideal blood oxygenation membrane, perfluoroesters of poly(ethylene-vinyl alcohol) copolymers have been made and found to be hydrolytically unstable under room temperature and ordinary atmospheric moisture conditions. These esterified copolymers are made by reacting the pendant hydroxyls of the vinyl alcohol units with perfluorobutyric acid chloride. Hydrolysis at room temperature in the presence of moisture at a pH of 7 regenerates free hydroxyl. For a report on the thrombo resistance of perfluoroacetate esters of poly(ethylene-vinyl alcohol), see Gott, NTIS annual report PB 186,551 (August, 1969), p. 65 et seq.

Fluorinated polyacrylate esters have also been investigated, in this case from the standpoint of gas permeability. Presently available data indicate that fluorination has no significant favorable effect upon the gas permeability of these acrylate polymers.

As illustrative of the state of the fluorinated film-forming polymer art, see British Pat. No. 1,120,373 (ICI, Ltd.), published July 17, 1968.

SUMMARY OF THE INVENTION

It has now been found that the gas permeability, blood compatibility, hydrophobicity, ease of manufacture, mechanical strength, handling properties, hydrolytic stability, and other desired properties for polymers used for gas permeable membranes and/or in the aforementioned biological environments can be effectively combined in essentially a single polymer structure derived from ethyl cellulose by acylation (i.e. esterification) of residual cellulose hydroxyls with fluorinated acylating agents (e.g. fluorinated acid halides). Apparently, the fluorinated esters of ethyl cellulose have not been previously recognized as having utility in fields requiring either blood compatibility or gas permeability.

The procedures and the usual starting materials for making fluorinated ester derivatives of ethyl cellulose are generally known. See British Pat. No. 1,120,373 (Park et al), published July 17, 1968. However, the synthesis disclosed in the Park et al patent is generally not geared to the esterification of all residual hydroxyls in ethyl cellulose. According to the objectives of Park et al, a fluorine content within the range of 0.1 to 10% by weight is adequate. Theoretically, this fluorine content can be obtained at a fraction of the stoichiometric requirements for esterification of free hydroxyls in the cellulosic polymer. In Example 7 of Park et al, the amount of perfluorooctanoic acid esterifying agent is approximately 5 mole % of stoichiometry, resulting in a purified product with a fluorine content of 2%.

Although this invention is not bound by any theory, it is presently theorized that residual hydroxyl groups in the ethyl cellulose molecule can participate in hydrogen bonding or similar effects which may, at some stage, be involved in thrombogenic behavior. Furthermore, it has now been discovered that, with respect to esterified ethyl cellulose, there is a positive correlation between the fluorine content (i.e. chemically combined fluorine content) of the ester groups and gas permeability. This discovery runs counter to some published findings with respect to some of the prior art gas permeable polymers, e.g. the siloxane type. In any event, fluoroacylated ethyl cellulose having a chemically combined fluorine content of less than about 12% by weight is not ordinarily preferred in this invention, although a fluorine content as low as 10.3% by weight is adequate for some of the purposes of this invention. By appropriately selecting the nature and amounts of starting materials used to make the fluoracylated ethyl cellulose polymers of this invention, it is possible to achieve a fluorine content of up to about 50% by weight, even with fluoroacylating agents derived from the most readily available materials.

The ethyl cellulose starting material selected for use in this invention normally averages about 2 to about 5.5 ethoxide groups per disaccharide unit, corresponding to a degree of substitution (D.S.) of 1.0 to 2.75. The upper end of the D.S. range is preferred, and ethyl cellulose with a D.S. of 2.2 or more is commercially available.

Ethyl cellulose derivatives used in this invention are film-forming and generally non-elastomeric. Thus, thin layers of these derivatives can be obtained in the form of films (e.g. solvent-cast films), membranes, coatings, etc. For coatings on gas impermeable substrates, the coating thickness is not critical, and about 1 mil (about 25 microns) or slightly less is adequate for continuous coverage. For purposes of blood oxygenation, thickness of about 0.5 mil (about 13 microns) or less are preferred. These derivatives can be formed into ultra-thin films or membranes (see Forester et al, U.S. Pat. No. 3,551,244, issued Dec. 29, 1970) 0.1 to 5 microns thick and used as blood oxygenating membranes or films, gas separation membranes or films, coatings on rigid, flat or cylindrical surfaces, or the like. Other areas of utility include biological implants, catheters, cannulas, artificial organs, blood filters, probes, devices for sampling and analysis of blood, and the like. The films, membranes, coatings, and other layers can be in the form of coils, laminates or composites, hollow fibers, or the like or can be placed in rigid frames. Chemical synthesis of the ethyl cellulose derivatives themselves and the film-forming or other related manufacturing steps connected with the manufacture of blood oxygenation devices and the like can be carried out in a reasonably straightforward manner. The mechanical strength properties of the polymer films are adequate for a variety of manufacturing procedures and uses of the resulting devices. The polymers can also be formed into fibers by known techniques, thus permitting the manufacture of fibrous woven or non-woven layers with somewhat greater flexibility than a cast film.

DETAILED DESCRIPTION

Figure 1:
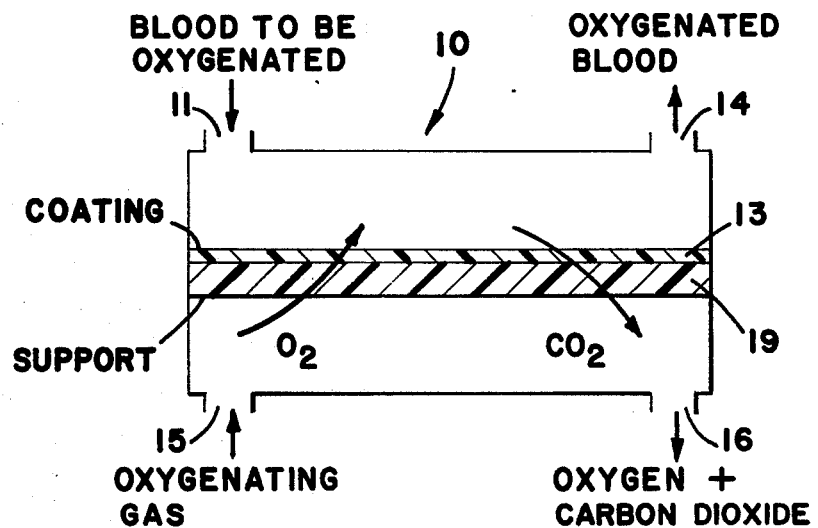
FIG. 1 is a fragmentary cross-sectional view of an embodiment of a blood oxygenation device comprising a blood compatible coating on a support means.

The starting materials for use in making fluoroacylated ethyl cellulose derivatives of this invention include the esterifying agent, the ethyl cellulose, and (in the case where the esterifying agent is an acid halide) a material for the uptake or removal of the hydrogen halide formed as a by-product of the synthesis. Suitable conventional solvents can be used to provide a medium for carrying out the reaction. Some of the preferred perfluorinated esterifying agents are disclosed in the aforementioned Park et al patent (British Pat. No. 1,120,373).

THE ESTERIFYING OR ACYLATING AGENT

All esterifying agents do not work with equal effectiveness, and the preferred esterifying agents can be represented by the formula $$R_f\text{---COX}$$

wherein $R_f$ is a fluorinated hydrocarbyl (e.g. aliphatic) radical and X is a halogen, preferably Cl. As pointed out in British Pat. No. 1,120,373, compounds are known in which $R_f$ can be a variety of perfluoroalkyl groups (typically straight-chain or cyclic perfluoroalkyls), e.g. perfluorobutyryl and perfluorooctanoyl. The corresponding carboxylic acids can be used (i.e. $R_f\text{COOH}$), but these compounds react somewhat slower and produce smaller yields. The corresponding acid anhydrides can also be used. Partially fluorinated acid halides are known.

A wide variety of fluorinated aliphatic groups has been reported in the patent and scientific literature. See, for example, the fluorocarbon "tail"-containing substituents disclosed in, U.S. Pat. No. 2,759,019, issued Aug. 14, 1956.

The lower perfluorinated alkyl compounds are generally the most readily available, although fluorohydrocarbons containing up to 33 carbon atoms can be made by known techniques. At the opposite end of the scale of carbon chain length, compounds containing the perfluoromethyl substituent are among the most commonly occuring in organic fluorine chemistry. However, in the context of this invention, perfluoromethyl esterifying agents (e.g. perfluoroacetic acid chloride) can be gases at room temperature and require more elaborate manufacturing procedures than the higher analogs, particularly the $C_4$ and higher acid chlorides, e.g. compounds of the formula $$CF_3(CF_2)_m COX$$

wherein $m$ is a number ranging from 2 to 10 (preferably 2 – 6), and X is a halide (e.g. Cl).

Despite the aforementioned manufacturing difficulties, however, perfluoroacetic acid chloride and perfluoropropionic acid chloride are fully operative in this invention.

From the standpoint of maximizing gas permeability of a membrane of the ethyl cellulose derivative with maximum ease of manufacture and mechanical strength of the film, the aforementioned range of $m$, particularly $m = 2$ through $m = 6$, appears to be optimum. A chemically combined fluorine content for the ethyl cellulose derivative which is in excess of 12% by weight can easily be achieved with these straight-chain perfluoroalkanoic acid halides. From the standpoint of the mechanical strength of ethyl cellulose derivative, the preferred range of $m$ is 1 through 6.

THE ETHYL CELLULOSE

As is known in the art, pure cellulose is a linear polymer made up of repeating saccharide (anhydroglucose) units linked at the 1- and 4- positions through beta-glycosidic bonds. The saccharide units can be considered to be repeating disaccharide units because of the alternating stereochemical orientation of the individual units. For film-forming properties, a typical minimum molecular weight for cellulose and its derivatives is about 20,000 Daltons. For convenience of processing, molecular weights above 100,000 are not ordinarily preferred. Accordingly, the number of hydroxyl groups etherified to form ethoxy substituents in the ethyl cellulose can be computed or averaged on either a per-saccharide or per-disaccharide basis. The per-saccharide basis is sometimes referred to as the Degree of Substitution (D.S.). Since the methylol substituent of the saccharide unit etherifies quite easily, it is difficult to achieve in practice a D.S. less than 1.0 (i.e. 2.0 per disaccharide unit). Commercially available ethyl cellulose materials typically have a D.S. above 2.0, e.g. 2.2 to about 2.75 (4.4 to about 5.5 ethoxy groups per disaccharide unit). In the context of this invention, there is no advantage in using ethyl cellulose materials which are outside of the commercially available range.

The commercial range of ethoxy content in ethyl cellulose can also be stated in terms of percent ethoxyl, and this typically ranges from about 45 to about 51% ethoxyl. Within the optimum limits described previously and hereinafter with regard to the selection of the nature and amounts of starting materials, variations in ethoxyl content (as well as perfluoroalkyl chain length) were found to have relatively insignificant effects upon gas transport rates and physical properties of the gas permeable films, membranes, coatings, etc.

The preferred range of average ethoxy content per disaccharide unit is about 4.4 to about 5.5. This means that essentially all of the pendant methylol groups and more than 50 mole % of the ring-substituted hydroxyls have been converted to ethoxide (ethyl ether) substituents. The residual hydroxyl content thus ranges from about 0.5 to about 1.6 OH/disaccharide unit, and these OH's should normally be substituents on the repeating saccharide rings. On the average, there is about one residual hydroxyl per disaccharide unit. However, perfectly uniform distribution of chemical functional groups throughout the cellulose polymer chain is not necessary in this invention, and, in any event, is extremely difficult to achieve in practice.

Needless to say, ethyl cellulose is one among many known cellulosic polymers, and a wide variety of other cellulosic polymers are known, including methyl cellulose, hydroxy ethyl cellulose, ethyl hydroxyethyl cellulose, carboxy methyl cellulose (and its salts), cellulose nitrate, cellulose acetate, mixed esters of cellulose, and the like. Of all these cellulosic materials, ethyl cellulose appears to represent the optimum starting material for a gas permeable membrane with fluorinated side chains and adequate mechanical strength.

SYNTHESIS OF FLUORINATED ETHYL CELLULOSE DERIVATIVES

Polymers useful in this invention are formed by the treatment of ethyl cellulose with the previously described acid halides or other esterifying agents. When acid halides are used (e.g. acid chlorides), it is preferred to provide a reaction medium containing an acid acceptor. Suitable acid acceptors are described on page 2, line 7 et seq. of British Pat. No. 1,120,373, the preferred acceptor being a compound which is or behaves like a tertiary amine, e.g. an aromatic heterocyclic amine such as pyridine. Suitable organic liquids for the reaction medium are known in the art, e.g. the chlorinated aliphatics such as methylene chloride, aromatic hydrocarbons such as toluene, and pyridine itself (both solvent and acid acceptor).

A simplified reaction scheme can be represented as follows:

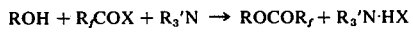

ROH + R$_f$COX + R$_3$'N → ROCOR$_f$ + R$_3$'N·HX wherein
ROH represents 1.0 hydroxyl equivalents of ethyl cellulose,
R$_f$ and X are as defined previously, and
R$_3$'N represents the amine acceptor for the hydrogen halide.

In this reaction scheme, the ratio of monocarboxylic esterifying agent to OH equivalents is shown as 1:1. In practice, an excess over stoichiometry of the esterifying agent is preferred, e.g. a 1 – 100% excess.

In a typical product, represented in the above equation by ROCOR$_f$, at least about 50 mole % (and even up to 100 mole %) of the repeating disaccharide units of the fluoroacylated ethyl cellulose derivative can have the following structural formula:

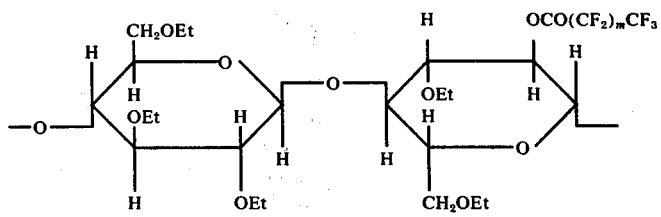

wherein the disaccharide units can be attached in a random head-to-head, head-to-tail arrangement, and wherein Et represents ethyl. As pointed out previously, the typical OCOR$_f$ substituent is a perfluoroalkanoyloxy group, i.e. a perfluoroalkanoyl ester. In the typical practice of this invention, the ester groups contain straight chain perfluoroalkanoyl groups of the formula CF$_3$(CF$_2$)$_m$CO—, wherein $m$ can be 0 and ordinarily need not be larger than 6, even for ethyl cellulose polymers with a relatively lower D.S. Good performance has been obtained with $m$ values ranging from 1 to 6, and, as pointed out previously, the compounds wherein $m$ equals 2 can be easier to make than the $m$ equals 0 and $m$ equals 1 species.

It is preferred that the fluoroacylated ethyl cellulose derivatives of this invention be substantially free of residual hydroxyls, as determined by infrared spectroscopic analysis. Typically, no more than a trace absorption is observed in the portions of the infrared spectrum for methylol groups and ring-substituted hydroxyl groups remaining on the ethyl cellulose molecule. Thus, within the limits of analytical error inherent in infrared spectroscopy, the preferred polymers of this invention are fully esterified and etherified and contain no more than trace quantities of free hydroxyl groups.

In the case of an ethyl cellulose with a very low degree of substitution (D.S.), residual hydroxyl groups can be esterified or otherwise blocked without converting every single OH into a $-OCOR_f$. For example, a mixture of esterifying agents can be used, wherein one or more of the esterifying agents contains no chemically combined fluorine. However, this approach is less convenient than the selection of a suitable D.S. ethyl cellulose and a suitable fluorinated esterifying agent. Furthermore, any procedure which would result in a low fluorine content (even if all residual OH were blocked) would not be preferred in this invention.

PHYSICAL PROPERTIES OF FLUOROACYLATED CELLULOSE FILMS OF THIS INVENTION

Ethyl cellulose itself has good film-forming properties and mechanical strength, but its gas permeability is well below the requirement for blood oxygenation devices and many other applications of gas permeable materials. For example, the gas permeability of a typical grade of ethyl cellulose is less than $20 \times 10^{-10}$ cm$^3$-cm/cm$^2$-sec-cm Hg for oxygen and about $85 \times 10^{10}$ or less (same units) for carbon dioxide. This performance can be as much as about one order of magnitude lower than prior art membranes specifically designed for gas permeability. However, these prior art gas permeable membranes (e.g., the polycarbonate-dimethylsilicone block copolymers) are also considered to lack blood compatibility.

Although some of the outstanding mechanical strength of ethyl cellulose is sacrificed when the ethyl cellulose is fluoroacylated according to the teachings of this invention, the losses are more than compensated for by the significant increase in blood compatibility and gas permeability. Polymeric films and membranes of this invention can provide a combination of properties extremely well suited to use in blood oxygenators and other devices which ordinarily require the use of thin films or coatings having blood compatibility, gas permeability, good mechanical strength, hydrolytic stability, and the like. When a self-supporting film of fluoroacylated ethyl cellulose is compared with the non-fluorinated ethyl cellulose from which it is derived, gas permeabilities (e.g. oxygen and carbon dioxide permeabilities) are increased by a factor ranging from about 1.9 to about 3.0. Gas transmission rates appear to increase slightly with increasing $m$ (defined previously) and/or increasing fluorine content. Mechanical strength properties, on the other hand, appear to decrease slightly with increasing $m$ and/or fluorine content. If the fluoroacylated ethyl cellulose is formed into an ultrathin film and combined with a suitable support which is permeable to gases and inert towards water, gas transmission rates for oxygen and carbon dioxide are superior, even when compared to reinforced silicone membranes. A typical laminate of the fluoroacylated ethyl cellulose used in this type of comparison comprises a nonwoven web such as a polyolefin paper (which can be made from staple or continuous polyolefin fiber by either a wet or dry process) laminated or bonded to an ultrathin film of fluoroacylated ethyl cellulose. One suitable lamination technique involves coating the inert porous substrate with a 1 to 20 micron layer of gas permeable adhesive (e.g., silicone adhesive) followed by lamination of the adhesive-coated substrate to the ultrathin film of fluoroacylated ethyl cellulose. Since the blood compatible fluoroacylated ethyl cellulose polymer completely covers the silicone adhesive and the porous substrate or support, an essentially non-thrombogenic surface is provided for contact with blood. The opposite side of the composite or laminate (which need not be blood compatible) provides a porous surface through which oxygen can be permeated and from which carbon dioxide carried by carboxyhemoglobin in the blood can be released. The mechanical strength properties of these laminates or composites are equal to or superior to a self-supporting film of the fluoroacylated ethyl cellulose itself. As is known in the art, it is not essential to use an adhesive to bond an ultrathin film to a support. Adequate gas permeability, blood compatibility, etc. can also be obtained for such adhesive-free laminates. Alternatively, a thin layer of the fluoroacylated ethyl cellulose can be directly deposited on the surface of a porous film or paper by various solvent coating processes.

Self-supporting films of fluoroacylated ethyl cellulose polymers used in this invention can have an ultimate tensile strength which is at least 25% of the parent ethyl cellulose polymer, more typically at least 30%. An ultimate tensile strength of at least 3000 p.s.i. ($2.1 \times 10^6$ kg/m$^2$) and a tensile modulus of at least 15,000 p.s.i. ($10.5 \times 10^6$ kg/m$^2$) can readily be achieved in practice. Ultimate tensile and modulus determinations were made using an Instron Tensile Testor according to ASTM D882-64T.

Ultimate tensile strength for the aforementioned ultrathin membrane/support laminates or composites can be in excess of 3500 p.s.i. ($2.4 \times 10^6$ kg/m$^2$) when the composite is wet or in excess of 4000 p.s.i. ($2.8 \times 10^6$ kg/m$^2$) when the composite is dry.

Fluoroacylation of ethyl cellulose does not decrease the elasticity of a film made from the polymer. If anything, elasticity is increased, even though the fluoroacylated polymers would not technically qualify as "elastomers". It is not unusual for polymeric films of this invention to have an elongation at break in excess of 40%.

The fluoroacylated ethyl cellulose has good hydrolytic stability at room temperature (20° – 25° C.), physiological temperatures (e.g. 35° – 40° C.) and sterilization temperatures (e.g. 100° C.). The pH of blood (7.4) also has little or no effect upon the hydrolytic stability of these polymers. Thus, the polymers have good chemical stability under room temperature conditions or mildly elevated temperature conditions in the presence of blood as well as water, saline solutions, and the like. No significant degradation was observed when polymeric films of this invention were exposed to boiling water at a pH of 7.4.

When implant rings were coated with polymers of this invention and then implanted in dogs, test results indicated that the implant thus prepared had about the same degree of blood compatibility as pyrolytic carbon, the most blood-compatible material currently known. (Pyrolytic carbon is a rigid, non-permeable material and has very few applications in implantable biomedical devices.)

BLOOD OXYGENATION DEVICES

The preferred blood oxygenation devices of this invention comprise a means for bringing blood (e.g., venous blood) of a living animal into contact with a major surface of a gas permeable membrane. For example, a suitable non-thrombogenic blood-conveying device can be used to tap into the circulatory system, and the blood from the circulatory system can be fed to a hollow fiber, a coil-like conduit, a series of spaces defined by gas-permeable surfaces, or the like. Essentially pure oxygen or oxygen mixed with carbon dioxide is brought into contact with the opposite major surface of the gas permeable coil, flat film or membrane, hollow fiber, or the like. Surfaces within the blood oxygenator device which are in contact with blood and require gas permeability are made from the fluoroacylated ethyl cellulose of this invention. The oxygen diffuses through the fluoroacylated ethyl cellulose into the blood, and the blood is permitted to release carbon dioxide.

Figure 2:
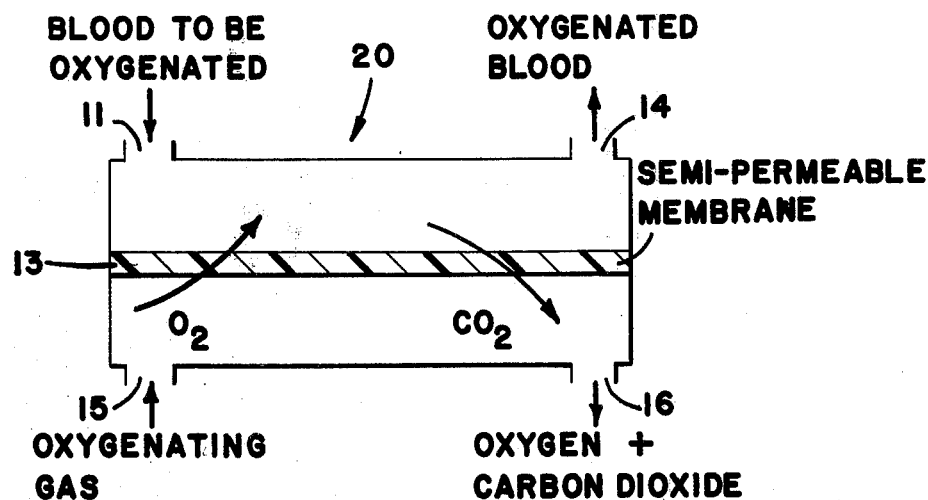
FIG. 2 is a fragmentary cross-sectional view of another embodiment of a blood oxygenation device.

Turning now to the Drawing, blood oxygenation device 10 (FIG. 1) or 20 (FIG. 2) comprises a means 11 for bringing blood of a living animal into contact with major surfaces 13 of a gas permeable membrane, and means 15 for bringing oxygen-containing gas into contact with the opposite major surface of a membrane 13 (as in FIG. 2) or the support means 19 (FIG. 1). The Drawing shows only a fragmentary cross-sectional view, since a series of spaces defined by membranes 13 can be provided. Membranes 13 are gas-permeable, blood-compatible ethyl cellulose derivatives of this invention. In FIG. 1, the membrane 13 is supported by gas permeable support means 19. That is, each laminate of membrane 13 and support means 19 (FIG. 1) comprises the fluoroacylated ethyl cellulose laminated or bonded to a substrate such as a non-woven web in accordance with the previous description of physical properties of fluoroacylated cellulose films of this invention. The oxygen diffuses through a membrane 13 into the blood, and the blood is permitted to release carbon dioxide, as described previously.

Blood oxygenation devices of this type using silicone membranes are known in the art. The blood passing through these prior art oxygenators is typically treated with an anti-clotting agent. In this invention, use of the anti-clotting agent appears to be unnecessary.

Blood-compatible material of this invention can also be used in the artificial lung or heart-lung machine type of oxygenator wherein the blood is brought directly into contact with oxygen gas. However, these devices utilize a method of oxygenation which can denature vital materials in the blood. Accordingly, the duration of use of these devices is typically limited to a few hours at best. In the preferred type of blood oxygenator devices, on the other hand, the blood is protected from denaturization, and such time limits need not be imposed.

The following Examples illustrate the principle and practice of this invention.

EXAMPLE 1
PREPARATION OF ETHYL CELLULOSE PERFLUOROBUTYRATE

In this Example, the ethyl cellulose had a Degree of Substitution of 2.55. One hundred grams of the ethyl cellulose (Grade T-50, 49.3% ethoxyl, Lot 42082 of Hercules, Inc.) was dried at 110° C. under vacuum. It was then dissolved in 1.25 Kg of methylene chloride at room temperature, followed by addition of 80 grams of dry pyridine. The solution was cooled at 10° C. A 20% excess of perfluorobutyryl chloride, 54 grams, based on calculated hydroxyl content of the ethyl cellulose, was added with stirring. Some warming occurred. After thirty minutes, the solution was poured into 3 liters of 70:30 methanol:water (on a volume basis) to precipitate the polymer. The supernatant solution was thoroughly decanted and the polymer was re-dissolved in 1.5 liters of acetone. The polymer was then re-precipitated in methanol-water, filtered, air-dried, then dried in vacuum at 90° C. The yield was 75% of theoretical.

EXAMPLE 2
PREPARATION OF OTHER PERFLUOROACYLATED ETHYL CELLULOSE POLYMERS

Six grades of ethyl cellulose ranging from 45.3 to 50.6 percent ethoxyl content (all obtained from Hercules, Inc.) were acylated with pentafluoropropionyl chloride, pentadecafluorooctanoyl chloride, and heptafluorobutyryl chloride. That is, the esterifying agents were characterized by the formula $CF_3(CF_2)_mCOCl$, wherein $m$ was 1, 2 and 6. The resulting polymers were made into films and tested for gas transport rates and physical properties (e.g., tensile strength). Variations in ethoxyl content and perfluoroalkyl chain length were found to have relatively minor effects upon gas transport rates and physical properties. Gas transport rates increased slightly with increasing fluorine content (i.e., perfluoroalkyl chain length) and mechanical strength properties decreased slightly with increasing fluorine content. For a mid-range ethoxyl content, the data for perfluorooctanoyl ethyl cellulose were as follows:

Gas permeability, $P \times 10^{10}$ wherein $P$ is in $cm^3$-$cm/cm^2$-sec-cm Hg:
Oxygen: 60
Carbon Dioxide: 210
Ultimate Tensile Strength, p.s.i.: 3450
Tensile Modulus, p.s.i.: 16,500
Percent Elongation at Break: 50–60%

The data for perfluoropropionyl ethyl cellulose were as follows:
Gas permeability, same units:
Oxygen: 50
Carbon Dioxide: 160
Ultimate Tensile Strength, p.s.i.: 3600
Tensile Modulus, p.s.i.: 20,000
Percent Elongation at Break: 50–60%

The mechanical strength properties of the above-described perfluorooctanoyl and the perfluoropropionyl ethyl cellulose are generally superior to other known gas permeable membranes (which are generally elastomeric), e.g. fluorosilicone polycarbonate-dimethylsilicone block copolymers, polysulfonedimethylsilicone block copolymers, and polyhexadecylsulfone, although the polysulfone-dimethylsilicone block copolymers are almost equal to the perfluorooctanoyl ethyl cellulose in ultimate tensile strength. None of these prior art gas permeable membranes is ordinarily considered to be blood compatible. Fluorosilicone elastomers have been suggested for use in blood oxygenation devices in combination with anti-clotting agents such as heparin. Gas permeabilities reported in the literature for these elastomers are high, e.g. (in $10^{10}$ $cm^3$-cm/$cm^2$-sec-cm Hg):

Oxygen: 124
Carbon Dioxide: 950
(as reported in the literature.)

The reported gas permeability data for polycarbonatedimethylsilicone block copolymer elastomers is slightly better.

EXAMPLE 3

ULTRATHIN MEMBRANES ON OLEFIN PAPER SUPPORTS

Two laminated samples were made from "Tyvek" 1073 (trademark for polyolefin paper), a gas permeable silicone adhesive. and an ultrathin layer of the perfluorobutyryl ethyl cellulose of Example 1. These laminated samples are hereinafter referred to as Examples 3(A) and 3(B). Example 3(A) was made by coating the "Tyvek" 1073 with a 5 to 10 micron-thick layer of Dow Corning No. 282 silicone adhesive and adhering a 1.0–1.5 micron layer of the Example 1 polymer to the silicone adhesive. Example 3(B) was made in the same manner, except that the layer of No. 282 silicone adhesive was 1.5–2 microns thick and the layer of Example 1 polymer was also 1.5–2 microns thick.

Gas transmission rates are reported in the following table.

|  | Gas Transmission Rate (cc/min-$m^2$-atm) | |
|---|---|---|
|  | Oxygen | Carbon Dioxide |
| Example 3(A) | 210 ± 50 | 1060 ± 90 |
| Example 3(B) | 470 ± 80 | 3610 ± 350 |
| Reinforced Silicone Membrane | 195 ± 25 | 1090 ± 230 |

The reinforced silicone membrane included in the table for comparison was taken from a "Sci-Med Kolobow"-type blood oxygenator. Its average thickness was 5 mils.

The ultimate tensile strength (tensile strength at break) was averaged for Example 3(A) and Example 3(B). Data were obtained on an Instron Tensile Tester according to ASTM Test D882-64T with a strain rate of 0.5 in/in/min. Since the "Tyvek" support was a web with a machine direction and a transverse direction, the tensile strength at break was determined for both directions. When the ultrathin membrane/adhesive/"Tyvek" composite was wet, the tensile strength was as follows:

Machine direction, p.s.i.: 4350 ± 580
Transverse direction, p.s.i.: 4910 ± 339

For the dry composite, tensile strength data were as follows:

Machine direction, p.s.i.: 4600 ± 570
Transverse direction, p.s.i.: 4950 ± 320

EXAMPLE 4

BLOOD COMPATIBILITY TESTS

In this Example, the perfluoroacyl ethyl cellulose tested was again the polymer of Example 1. Implant rings were coated with the polymer and implanted in dogs. Two different types of ring tests were used: the UBTL Gott Ring Test (used to test primarily thrombus formation toward venous blood) and the Renal Embolus Ring Test (to test thromboemboli formation toward arterial blood). The results of the tests are reported in Tables I and II, below

TABLE I

UBTL Gott Ring Tests of Example 1 Polymer

| Sterilization Method | Number of Specimens Exhibiting Each Level of Thrombus Formation* | | |
|---|---|---|---|
|  | 0 | 1 | X |
| Autoclave | 3 | 0 | 0 |
| Ethylene oxide | 1 | 2 | 0 |

*Level 0 = No clots or small clots
Level 1 = Intermediate clots, no appreciable reduction in flow
Level X = Total or nearly total occlusion

TABLE II

RENAL EMBOLUS RING TESTS

| Dog No. | Duration | Ring Thrombus Code* | Aorta Below Ring | Kidney Infarcts |
|---|---|---|---|---|
| 1 | 5 days | 1— | Clean, undamaged. | Rt: 2 infarcts, >2 cm. Left: 2 infarcts, +3 mm. |
| 2 | 4 days | 1— | Clean, undamaged. | Rt: ± 50% infarct damage. Left: 2 infarcts, 2–3 mm. |
| 3 | 4 days | 0 | Clean, undamaged. | Rt: 1 infarct, ± 4 mm. Left: 1 infarct, ± 2 mm. |
| 4 | 3 days | 0 | Clean, undamaged. | Rt: 6 infarcts, up to >2 cm. Left: 3 infarcts, up to 1 cm. |

*Ring Thrombus Code
0. None.
1. Thin coating on ring lumen and/or skimpy deposit on the rim/aortic wall.
2. Thin coating on ring lumen which projects from ring in form of tube or flag.
3. Thickened deposit on all or part of ring lumen which markedly reduces size of lumen and may extend from ring to block or partially block a renal artery.
4. Any thrombus which completely occludes ring.

I claim:

1. In a blood oxygenation device comprising a means for bringing blood into contact with a gas-permeable support means and a means for conveying oxygenating gas to the other side of the gas-permeable support means, the improvement which comprises: a coating comprising fluoroacylated ethyl cellulose as a gas-permeable coating on said gas-permeable support means and for being in contact with the blood; wherein said fluorinated ethyl cellulose has a calculated chemically combined fluorine content of at least about 10% by weight and a degree of substitution ranging from about 1.0 to about 2.75, and wherein substantially all residual hydroxyls, including ring-substituted hydroxyls, have been converted to fluorinated ester groups of the formula —OCO(CF$_2$)$_m$CF$_3$, wherein $m$ is a number ranging from 1 to 6; said fluoroacylated ethyl cellulose containing, at most, trace amounts of residual hydroxyl groups as determined by infrared analysis.

2. Device according to claim 1, wherein said fluoroacylated ethyl cellulose has a chemically combined fluorine content of at least about 12% by weight.

3. Device according to claim 2, wherein said fluoroacylated ethyl cellulose averages about 0.5 to 1.6 perfluoroalkanoyl ester groups per disaccharide unit, said fluoroacylated ethyl cellulose having an ultimate tensile strength of at least 3000 pounds per square inch, a tensile modulus of at least 15,000 pounds per square inch, and more than twice the permeability to gaseous oxygen of the corresponding non-fluoroacylated ethyl cellulose.

4. A blood oxygenation device comprising:
means for bringing blood of a living animal into contact with a major surface of a gas permeable membrane, and
means for bringing oxygen gas into contact with the opposite major surface of said gas permeable membrane, said gas permeable membrane comprising an ethyl cellulose derivative which has a degree of substitution ranging from about 1.0 to about 2.75 and wherein substantially all residual hydroxyls, including substantially all ring-substituted hydroxyls, have been converted to fluorinated ester groups of the formula —OCO(CF$_2$)$_m$CF$_3$, wherein $m$ is a number ranging from 1 to 6, said ethyl cellulose derivative containing, at most, trace amounts of residual hydroxyl groups as determined by infrared spectroscopic analysis; said ethyl cellulose derivative having a calculated chemically combined fluorine content of at least about 10% by weight.

5. A blood oxygenation device according to claim 4, wherein said ethyl cellulose derivative has about 4.4 to about 5.5 ethoxide groups and about 0.5 to about 1.0 perfluorobutyrate groups per disaccharide unit of said ethyl cellulose derivative, said ethyl cellulose derivative having a fluorine content of at least about 12% by weight.

* * * * *